(12) United States Patent
Nie et al.

(10) Patent No.: US 11,092,534 B2
(45) Date of Patent: Aug. 17, 2021

(54) METHOD FOR DETECTING CONCENTRATION OF PARTICLES IN FLUID

(71) Applicant: FATRI UNITED TESTING & CONTROL (QUANZHOU) TECHNOLOGIES CO., LTD., Fujian (CN)

(72) Inventors: Yongzhong Nie, Fujian (CN); Zhongping Zhang, Fujian (CN)

(73) Assignee: FATRI UNITED TESTING & CONTROL (QUANZHOU) TECHNOLOGIES CO., LTD., Quanzhou (CN)

( * ) Notice: Subject to any disclaimer, the term of this patent is extended or adjusted under 35 U.S.C. 154(b) by 0 days.

(21) Appl. No.: 16/487,941

(22) PCT Filed: Nov. 30, 2018

(86) PCT No.: PCT/CN2018/118699
§ 371 (c)(1),
(2) Date: Aug. 22, 2019

(87) PCT Pub. No.: WO2019/109874
PCT Pub. Date: Jun. 13, 2019

(65) Prior Publication Data
US 2020/0340902 A1 Oct. 29, 2020

(30) Foreign Application Priority Data
Dec. 5, 2017 (CN) .......................... 201711269390.2

(51) Int. Cl.
*G01N 15/06* (2006.01)
(52) U.S. Cl.
CPC ..... *G01N 15/06* (2013.01); *G01N 2015/0693* (2013.01)
(58) Field of Classification Search
CPC ........... G01N 15/06; G01N 2015/0693; G01N 15/1459; G01N 2015/0053;
(Continued)

(56) References Cited

U.S. PATENT DOCUMENTS

| 2004/0011975 A1 | 1/2004 | Nicoli et al. |
| 2012/0140223 A1 | 6/2012 | Mitchell et al. |

(Continued)

FOREIGN PATENT DOCUMENTS

| CN | 1682105 | 10/2005 |
| CN | 101655457 | 2/2010 |

(Continued)

OTHER PUBLICATIONS

International Search Report for International Application PCT/CN2018/118699, dated Feb. 27, 2019.

(Continued)

*Primary Examiner* — Tri T Ton
(74) *Attorney, Agent, or Firm* — Burris Law, PLLC

(57) ABSTRACT

A method for detecting the concentration of particles in a fluid is disclosed. The method comprises the steps of: S1: introducing a pure fluid into a detection device to obtain a scatter background noise value U noise output by the detection device; S2: introducing a fluid to be detected into the detection device, obtaining scatter signals output by the detection device, and obtaining voltage signals of standard particles; S3: sampling signals of the fluid in a certain period of time, extracting effective signals, carrying out threshold value analysis on the effective signals Ux obtained by sampling, and obtaining the number of particles present in the period of time; and S4: obtaining the concentration of the particles in the fluid according to the number of particles in S3. According to this method, the accuracy in calculation of the concentration of particles in a fluid can be effectively improved.

5 Claims, 1 Drawing Sheet

---

Figure 1:
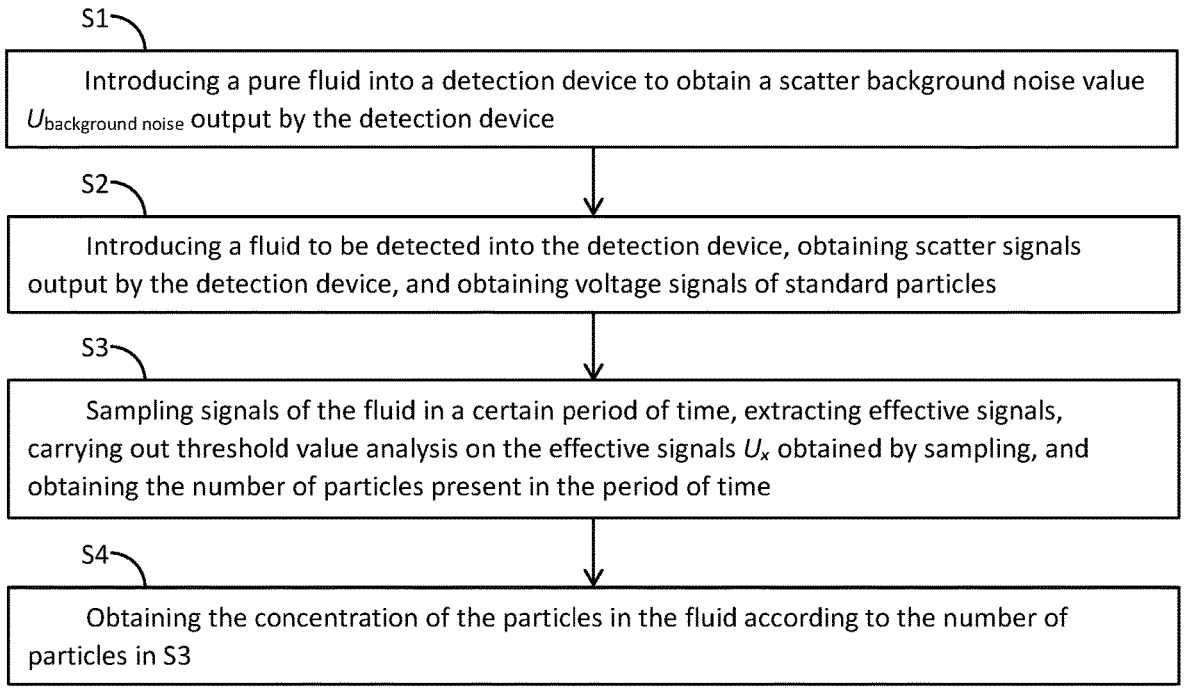

S41
Calculating the volume $V_x$ of the particles:

$$V_x = K \times V_{10\,\mu m} \times \sqrt{\frac{U_x - U_{\text{background noise}}}{U_{10\,\mu m} - U_{\text{background noise}}}}$$

where $V_x$ represents volume of unknown particles; $K$ represents a sensor correction coefficient; $V_{10\,\mu m}$ represents standard particle volume; $U_x$ represents output voltage amplitude of an unknown volume of particles; $U_{10\,\mu m}$ represents output voltage amplitude of standard particles S42
Obtaining the concentration of the particles in the fluid:
Obtaining the fluid flow velocity $v$, the cross-sectional area $S$ of the detection pipeline, converting the number and volume of particles passing through the pipeline in a period of time $t$ into a total mass $m$, and obtaining the particle concentration $c$ through the following formula:

$$c = \frac{m}{v \times t \times S}\,(\mu g / m^3)$$

(58) Field of Classification Search
CPC ... G01N 2015/1043; G01N 2015/1486; G01N 33/2858
USPC ................................................ 356/335–343
See application file for complete search history.

(56) References Cited

U.S. PATENT DOCUMENTS

2014/0152986 A1* 6/2014 Trainer .............. G01N 15/0211
356/336
2015/0121994 A1  5/2015 Wilhelm

FOREIGN PATENT DOCUMENTS

| | | |
|---|---|---|
| CN | 101762447 | 6/2010 |
| CN | 101925809 | 12/2010 |
| CN | 103163050 | 6/2013 |
| CN | 103792166 | 5/2014 |
| CN | 105842142 | 8/2016 |
| CN | 108169086 | 6/2018 |
| WO | 2014005673 | 1/2014 |

OTHER PUBLICATIONS

Zhou Shisheng, Mechanical Repairing and Installation, Metallurgical Industry Press, Sep. 2001, p. 204, 2nd to 11th paragraphs.
Office Action issued to Chinese counterpart application No. 201711269390.2 dated Apr. 19, 2019.

* cited by examiner

METHOD FOR DETECTING CONCENTRATION OF PARTICLES IN FLUID

CROSS-REFERENCE TO RELATED APPLICATIONS

This application is a U.S. national phase application of International Application No. PCT/CN2018/118699, filed on Nov. 30, 2018, which claims priority to and the benefit of Chinese Patent Application No. 201711269390.2, filed on Dec. 5, 2017. The disclosures of the above applications are incorporated herein by reference.

FIELD

The present disclosure relates to the technical field of detection device, in particular to a method for detecting the concentration of particles in a fluid.

BACKGROUND

The statements in this section merely provide background information related to the present disclosure and may not constitute prior art.

In order to reduce wear loss during operation of engine, bearing, gear and so on, it is often necessary to equip lubricating oil system, but factors such as impurities and debris will bring great disaster. Failure in operation of large-scale mechanical equipment is often due to a vicious cycle caused by the accumulation of abrasive debris in lubricating oil. In a wear failure diagnosis system, there is a strong correlation between the degree of damage to wear components (such as engines, rolling bearings, gears, etc.) and particles in the lubrication system. In order to realize the detection of lubricating oil particles, a particle form detection device, such as a fluid transparency detection device, is usually installed in a lubricating oil pipeline at first to monitor the lubricating oil quality on line in real time, and provide an effective basis for the failure diagnosis of an engine, a bearing, a gear and the like, thereby quickly and accurately figuring out the abrasion state and the failure reason of the equipment.

However, in the prior art of the fluid particle concentration detection method, the elimination of the influence on the background noise value of the fluid is absent, so that the subsequent calculation of the particle concentration may have a large error, and the accuracy of concentration calculation is affected; in addition, there are also defects in the selection of standard particles, as a result the measurement accuracy and sensitivity cannot be both considered in the measurement process; finally, the influence of the background noise value is not corrected when the concentration is calculated, therefore the accuracy of measurement is further affected.

SUMMARY

In order to overcome the defects of the prior art, the technical problem to be solved by the invention is how to provide a detection method for more accurately measuring the concentration of particles in a fluid.

In order to solve the technical problem, the technical solution adopted by the invention specifically comprises the steps of:

S1: introducing a pure fluid into a detection device to obtain a scatter background noise value $U_{background\ noise}$ output by the detection device;

S2: introducing a fluid to be detected into the detection device, obtaining scatter signals output by the detection device, and obtaining voltage signals of standard particles;

S3: sampling signals of the fluid in a certain period of time, extracting effective signals, carrying out threshold value analysis on the effective signals $U_x$ obtained by sampling, and obtaining the number of particles present in the period of time; and S4: obtaining the concentration of the particles in the fluid according to the number of particles in S3.

It should be noted that, in order to overcome the above-mentioned defects in the prior art mentioned in the background, the inventor has made several improvements to the method for detecting the concentration of particles in a fluid, including obtaining a scatter background noise value $U_{background\ noise}$ output by a detection device, and removing the influence caused by the background noise value in a subsequent detection calculation process, thereby improving the accuracy of the detection and calculation of the concentration of particles in the fluid.

It should be noted that the certain period of time may refer to any period of time, which may be chosen according to the actual situation.

Preferably, the standard particles are selected from particles having a diameter of 10 μm, with a corresponding voltage signal of $U_{10\ \mu m}$.

In the technical solution, particles with a diameter of 10 μm are preferably selected as standard particles, so that on one hand the detection accuracy can be improved, and on the other hand the detection sensitivity can be improved. If the particles are too large, the detection accuracy for the subsequent concentration calculation is decreased, and if the particles are too small, the detection sensitivity of the device is decreased, as a result the particle detection may fail. Therefore, the detection accuracy and the detection sensitivity can be effectively balanced by taking particles with a diameter of 10 μm as standard particles by the inventor, thereby rendering a more accurate detection process.

Preferably, the effective signal is extracted by comparing the sampled signals with the scatter background noise value, and selecting signals greater than the scatter background noise value as effective signals.

In the technical solution, it's necessary to select an effective signal as a basis for subsequent calculation, otherwise the accuracy of the detection and calculation results would be affected. The inventor selects a simple and effective method for selecting an effective signal, namely the sampled signals are compared with the previously obtained scatter background noise value, and signals greater than the scatter background noise value are used as the effective signals, so that the sampled signals show more practicability, and the subsequent measurement result is more accurate.

Preferably, the step of obtaining the number of particles through a threshold analysis in S3 comprises the step of:

comparing the obtained signal $U_x$ with a background noise value $U_{background\ noise}$, if $U_x - U_{background\ noise} > 0$, adding 1 to the count, and if $U_x - U_{background\ noise} < 0$, the count being zero.

In this step, as to the counting method, the inventor chooses preferably to compare the signal value with the background noise value instead of directly taking read-out values of the signal as the count, so that errors caused by the background noise value can be eliminated, that is, only signals when $U_x - U_{background\ noise} > 0$ are counted as representing particles, thereby rendering a more accurate detection result and an improved detection accuracy of the concentration of the particles.

Preferably, the step to obtain the particle concentration in S4 comprises the steps of:

S41: calculating the volume $V_x$ of the particles:

$$V_x = K \times V_{10\mu m} \times \sqrt{\frac{U_x - U_{background\ noise}}{U_{10\mu m} - U_{background\ noise}}}$$

where $V_x$ represents volume of unknown particles; K represents a sensor correction coefficient; $V_{10\ \mu m}$ represents standard particle volume; $U_x$ represents output voltage amplitude of an unknown volume of particles; $U_{10\ \mu m}$ represents output voltage amplitude of standard particles; and S42: obtaining the concentration of the particles in the fluid:

obtaining the fluid flow velocity v, the cross-sectional area S of the detection pipeline, converting the number and volume of particles passing through the pipeline in a period of time t into a total mass m, and obtaining the particle concentration c through the following formula:

$$c = \frac{m}{v \times t \times S}(\mu g/m^3)$$

It should be noted that the sensor correction coefficient K is introduced herein for the situation that in the calibration and use of the sensor, a background noise calibration offset may inevitably occur and generate errors in measurement, the correction coefficient K can be fine-tuning in this situation; it is also possible that when standard particles are selected, the particles are not completely standard, resulting in some subtle volume calculation errors, in this case, the errors can also be corrected by introducing the correction coefficient K.

In this step, elimination the influence of the background noise value is also taken into consideration, so that the detection result is more accurate. As in the above-mentioned calculation formula of the particles, factors of subtracting $U_{background\ noise}$ from $U_x$ and subtracting $U_{background\ noise}$ from $U_{10\ \mu m}$, thereby rendering a calculated volume of the particles closer to the actual value, and improving the calculation accuracy of the concentration of the particles in the fluid.

Compared with the prior art, the invention has the following advantages:

1. According to the fluid particle concentration detection method of the present invention, in the step of calculating the particle concentration, elimination of the influence of the background noise value is taken into consideration, thereby rendering a calculated volume of the particles closer to the actual value, and improving the calculation accuracy of the concentration of the particles in the fluid;

2. According to the fluid particle concentration detection method of the present invention, particles with a diameter of 10 μm are selected as standard particles, so that on one hand the detection accuracy can be improved, and on the other hand the detection sensitivity can be improved;

3. According to the fluid particle concentration detection method of the present invention, the sampled signals are compared with the previously obtained scatter background noise value, and signals greater than the scatter background noise value are used as the effective signals, so that the sampled signals show more practicability, and the subsequent measurement result is more accurate;

4. According to the fluid particle concentration detection method of the present invention, as to the counting method, the inventor chooses preferably to compare the signal value with the background noise value instead of directly taking read-out values of the signal as the count, thereby rendering a more accurate detection result and an improved detection accuracy of the concentration of the particles.

The above description is merely a summary of the technical solutions of the present invention, in order to render a more clear understanding of the technical means of the present invention to implement according to the content of the description, and in order to render the above and other objects, features and advantages of the present invention to be more readily understood, the following detailed description of the preferred embodiments is carried out taken in conjunction with the accompanying drawings.

Further areas of applicability will become apparent from the description provided herein. It should be understood that the description and specific examples are intended for purposes of illustration only and are not intended to limit the scope of the present disclosure.

DRAWINGS

Figure 2:
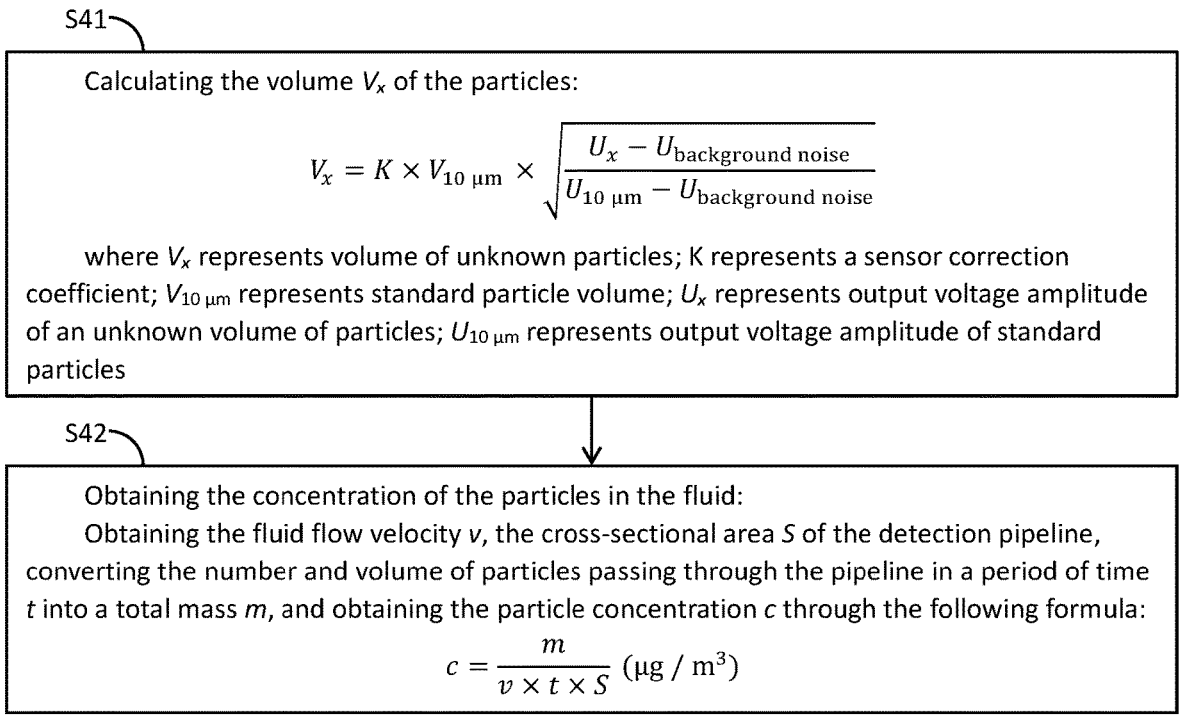

FIG. 1 is a flow chart of a method for detecting the concentration of particles in a fluid according to an embodiments of the present application; and FIG. 2 is a flow chart of a step of obtaining the concentration of the particles in the fluid in the method as shown in FIG. 1.

DETAILED DESCRIPTION

The following description is merely exemplary in nature and is not intended to limit the present disclosure, application, or uses. It should be understood that throughout the drawings, corresponding reference numerals indicate like or corresponding parts and features.

In order to further illustrate the technical means of the present invention for achieving the intended purposes thereof as well as effects, the following detailed description is made, taken in conjunction with the accompanying drawings and preferred embodiments, to illustrate specific embodiments, structures, features and efficacy thereof according to the present invention.

The invention discloses a method for detecting the concentration of particles in a fluid, as shown in FIG. 1, comprising the steps of:

S1: introducing a pure fluid into a detection device to obtain a scatter background noise value $U_{background\ noise}$ output by the detection device;

S2: introducing a fluid to be detected into the detection device, obtaining scatter signals output by the detection device, and obtaining voltage signals of standard particles;

S3: sampling signals of the fluid in a certain period of time, extracting effective signals, carrying out threshold value analysis on the effective signals $U_x$ obtained by sampling, and obtaining the number of particles present in the period of time; and S4: obtaining the concentration of the particles in the fluid according to the number of particles in S3.

A scatter background noise value $U_{background\ noise}$ output by a detection device is obtained, and the influence caused by the background noise value in a subsequent detection calculation process is removed, thereby improving the accuracy of the detection and calculation of the concentration of particles in the fluid.

In combination with the above embodiments, in one preferred embodiment thereof, the standard particles are selected from particles having a diameter of 10 μm, with a corresponding voltage signal of $U_{10\ \mu m}$.

In the actual selection process of the standard particles, if the particles are too large, the detection accuracy for the subsequent concentration calculation is decreased, and if the particles are too small, the detection sensitivity of the device is decreased, as a result the particle detection may fail. Therefore, the detection accuracy and the detection sensitivity can be effectively balanced by taking particles with a diameter of 10 μm as standard particles by the inventor, on one hand the detection accuracy can be improved, and on the other hand the detection sensitivity can be improved.

In combination with the above embodiments, in one preferred embodiment thereof, the effective signal is extracted by comparing the sampled signals with the scatter background noise value, and selecting signals greater than the scatter background noise value as effective signals.

The sampled signals are compared with the previously obtained scatter background noise value, and signals greater than the scatter background noise value are used as the effective signals, so that the sampled signals show more practicability, and the subsequent measurement result is more accurate.

In combination with the above embodiments, in one preferred embodiment thereof, the step of obtaining the number of particles through a threshold analysis in S3 comprises the step of:

comparing the obtained signal $U_x$ with a background noise value $U_{background\ noise}$, if $U_x - U_{background\ noise} > 0$, adding 1 to the count, and if $U_x - U_{background\ noise} < 0$, the count being zero.

In this step, as to the counting method, the inventor chooses preferably to compare the signal value with the background noise value instead of directly taking read-out values of the signal as the count, so that errors caused by the background noise value can be eliminated, that is, only signals when $U_x - U_{background\ noise} > 0$ are counted as representing particles, thereby rendering a more accurate detection result and an improved detection accuracy of the concentration of the particles.

In combination with the above embodiments, in another preferred embodiment, the step to obtain the particle concentration in S4, as shown in FIG. 2, comprises the steps of:

S41: calculating the volume $V_x$ of the particles:

$$V_x = K \times V_{10\mu m} \times \sqrt{\frac{U_x - U_{background\ noise}}{U_{10\mu m} - U_{background\ noise}}}$$

where $V_x$ represents volume of unknown particles; K represents a sensor correction coefficient; $V_{10\ \mu m}$ represents standard particle volume; $U_x$ represents output voltage amplitude of an unknown volume of particles; $U_{10\ \mu m}$ represents output voltage amplitude of standard particles; and S42: obtaining the concentration of the particles in the fluid:

Obtaining the fluid flow velocity v, the cross-sectional area S of the detection pipeline, converting the number and volume of particles passing through the pipeline in a period of time t into a total mass m, and obtaining the particle concentration c through the following formula:

$$c = \frac{m}{v \times t \times S} (\mu g/m^3)$$

In this step, elimination the influence of the background noise value is also taken into consideration, so that the detection result is more accurate. As in the above-mentioned calculation formula of the particles, factors of subtracting $U_{background\ noise}$ from $U_x$ and subtracting $U_{background\ noise}$ from $U_{10\ \mu m}$, thereby rendering a calculated volume of the particles closer to the actual value, and improving the calculation accuracy of the concentration of the particles in the fluid.

The total mass m is calculated as follows:
Calculation of the mass of a single particle $$m = \rho \times V$$

The particle herein is regarded by default as a common particle in the fluid, a relative density of the particle is substituted into the above formula and the mass of a single particle can be obtained through conversion.

Accumulation of masses of particles in a period of time is performed on the basis of calculation of the mass of a single particle to obtain the total mass of the particles in the current period of time:

$$M = \sum_{i=1}^{N} m_i$$

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice; material, manufacturing, and assembly tolerances; and testing capability.

As used herein, the phrase at least one of A, B, and C should be construed to mean a logical (A OR B OR C), using a non-exclusive logical OR, and should not be construed to mean "at least one of A, at least one of B, and at least one of C."

The above-described embodiments are merely preferred embodiments of the present invention, and thus do not limit the scope of the present invention, and any insubstantial changes and substitutions made by those skilled in the art based on the present invention are intended to be within the scope of the present invention.

What is claimed is:

1. A method for detecting concentration of particles in a fluid, comprising steps of:
   S1: introducing a pure fluid into a detection pipeline to obtain a scatter background noise value $U_{background\ noise}$ output by the detection pipeline;
   S2: introducing a fluid to be detected into the detection pipeline, obtaining scatter signals output by the detection pipeline, and obtaining voltage signals of standard particles;
   S3: sampling signals of the fluid in a period of time and obtaining signals $U_x$ of an unknown volume of the particles, extracting signals greater than the scatter background noise value, carrying out a threshold value analysis on the signals $U_x$ obtained by sampling, and obtaining a number of particles present in the period of time; and S4: obtaining concentration of the particles in the fluid according to the number of the particles in S3, fluid flow velocity v, cross-sectional area S of the detection pipeline, and number and volume of the particles passing through the detection pipeline in a period of time t.

2. The method according to claim 1, wherein the standard particles are selected from particles having a diameter of 10 μm, with a corresponding voltage signal of $U_{10\ \mu m}$.

3. The method according to claim 1, wherein the signals greater than the scatter background noise value is extracted by comparing sampled signals with the scatter background noise value.

4. The method according to claim 1, wherein the step of obtaining the number of the particles through the threshold analysis in S3 comprises step of:

comparing the obtained signal $U_x$ with the background noise value $U_{background\ noise}$, if $U_x - U_{background\ noise} > 0$, adding 1 to a count, and if $U_x - U_{background\ noise} < 0$, the count being zero.

5. The method according to claim 1, wherein the step for obtaining the particle concentration in S4 comprises steps of:

S41: calculating volume $V_x$ of the unknown particles:

$$V_x = K \times V_{10\mu m} \times \sqrt{\frac{U_x - U_{background\ noise}}{U_{10\mu m} - U_{background\ noise}}}$$

where $V_x$ represents volume of unknown particles; K represents a sensor correction coefficient; $V_{10\ \mu m}$ represents volume of the standard particles; $U_x$ represents output voltage amplitude of an unknown volume of the particles; $U_{10\ \mu m}$ represents output voltage amplitude of the standard particles; and S42: obtaining the concentration of the particles in the fluid:

obtaining said fluid flow velocity v, said cross-sectional area S of the detection pipeline, converting said number and said volume of the particles passing through the detection pipeline in the period of time t into a total mass m, and obtaining particle concentration c through the following formula:

$$c = \frac{m}{v \times t \times S} (\mu g/m^3).$$

\* \* \* \* \*